United States Patent
Renta

(10) Patent No.: US 9,756,419 B2
(45) Date of Patent: Sep. 5, 2017

(54) POWER STETHOSCOPE WITH INTEGRATED SPEAKER

(71) Applicant: Antonio Renta, Belle Isle, FL (US)

(72) Inventor: Antonio Renta, Belle Isle, FL (US)

(*) Notice: Subject to any disclaimer, the term of this patent is extended or adjusted under 35 U.S.C. 154(b) by 0 days.

(21) Appl. No.: 15/071,927

(22) Filed: Mar. 16, 2016

(65) Prior Publication Data

US 2016/0366514 A1 Dec. 15, 2016

Related U.S. Application Data

(60) Provisional application No. 62/174,698, filed on Jun. 12, 2015.

(51) Int. Cl.
*A61B 7/04* (2006.01)
*H04R 1/46* (2006.01)
*H04R 1/34* (2006.01)

(52) U.S. Cl.
CPC ............. *H04R 1/46* (2013.01); *A61B 7/04* (2013.01); *H04R 1/342* (2013.01)

(58) Field of Classification Search
CPC ............. A61B 7/04; A61B 7/02; H04R 1/46
USPC .......................................................... 381/67
See application file for complete search history.

(56) References Cited

U.S. PATENT DOCUMENTS

| | | | | |
|---|---|---|---|---|
| 8,909,879 B2* | 12/2014 | Bonanno | ............ | G06F 12/00 |
| | | | | 711/156 |
| 9,414,803 B1* | 8/2016 | Naqvi | ............ | A61B 7/04 |
| 2005/0014999 A1* | 1/2005 | Rahe-Meyer | ...... | A61B 5/01 |
| | | | | 600/323 |
| 2007/0058818 A1* | 3/2007 | Yoshimine | ........ | A61B 7/04 |
| | | | | 381/67 |
| 2012/0283598 A1* | 11/2012 | Horii | ................ | A61B 5/087 |
| | | | | 600/586 |
| 2015/0156583 A1* | 6/2015 | Mulumudi | ........ | H04R 1/46 |
| | | | | 381/67 |
| 2015/0190110 A1* | 7/2015 | Chong | ............. | H04R 1/46 |
| | | | | 600/528 |

* cited by examiner

*Primary Examiner* — Disler Paul
(74) *Attorney, Agent, or Firm* — Jason T. Daniel, Esq.; Daniel Law Offices, P.A.

(57) ABSTRACT

A power stethoscope with integrated speaker includes a compact main body that houses a microphone, a speaker and a sound funnel. The sound funnel has a cap along the bottom end that permits the passage of sound waves for capture by the microphone. A control unit having a processor, a memory and a digital filter is communicatively linked to the microphone and speaker. The memory can record the microphone output, and a communication can transmit the same to an external device.

12 Claims, 3 Drawing Sheets

POWER STETHOSCOPE WITH INTEGRATED SPEAKER

CROSS-REFERENCE TO RELATED APPLICATIONS

This application claims the benefit of U.S. Application Ser. No. 62/174,698 filed on Jun. 12, 2015, the contents of which are incorporated herein by reference.

TECHNICAL FIELD

The present invention relates generally to medical instruments, and more particularly to an electronic stethoscope having an integrated microphone and speaker.

BACKGROUND

The statements in this section merely provide background information related to the present disclosure and may not constitute prior art.

One of the most recognizable medical instruments is the stethoscope, which can be found on or about virtually any medical professional. Although stethoscopes are a staple of the medical community, their design has changed little in more than 100 years. In this regard, conventional stethoscopes utilize a diaphragm that naturally conducts sound through rubber tubing that terminates into binaural earplugs.

Although these devices work well in the relatively quiet environment of a doctor's office, they are known to be difficult to use in high noise areas such as emergency rooms, trauma centers, and moving vehicles such as ambulances, and/or medical transport aircraft, for example. For these locations, practitioners must utilize specialized medical equipment such as electrocardiographic heart monitors, for example, which utilize a plurality of individual leads that must be accurately positioned on or about the patient's body. Unfortunately, the large size and high cost of such machines means that they are not always available for use when needed by a medical professional.

Accordingly, it would be beneficial to provide a low cost lightweight power stethoscope with an integrated audio output mechanism that does not suffer from the drawbacks of the above noted devices.

SUMMARY OF THE INVENTION

The present invention is directed to a power stethoscope. One embodiment of the present invention can include a compact main body that houses a microphone, a speaker and a sound funnel. Patient sounds can pass through the funnel to be captured by the microphone and played for a user via the speaker. The stethoscope can also include a control unit having a processor and memory for storing the sound captured by the microphone. This information can be transmitted to other devices via a communication port that is also in communication with the processor.

In another embodiment, the device can also include a digital audio filter that can process the captured sound to ensure an accurate representation of the same via the speaker, and a power source for providing the necessary power requirements for each device component.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1:
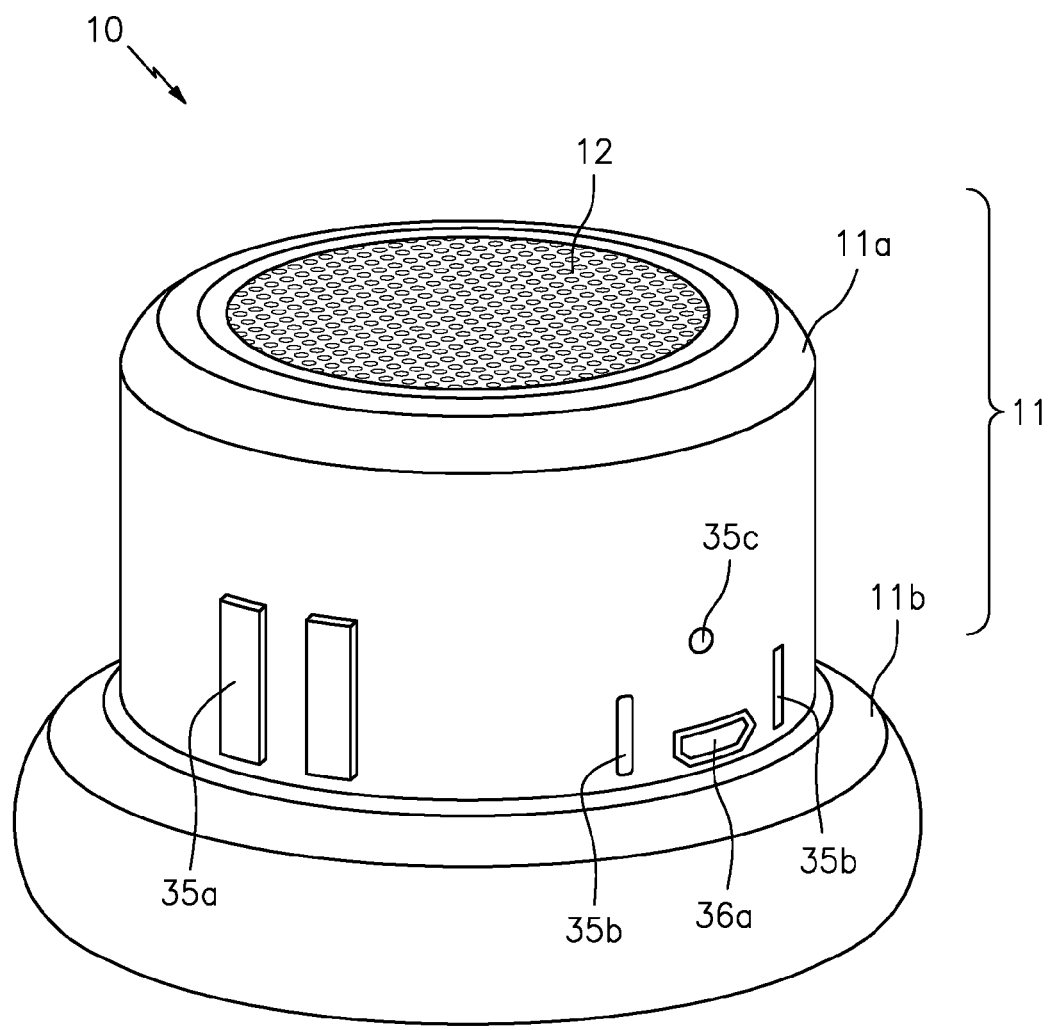
FIG. 1 is a perspective view of the power stethoscope with integrated speaker that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

As described throughout this document, the terms "patient sounds" and "sound waves" can be used interchangeably to describe any type of sound to be captured by the device microphone for playback by the speaker.

Figure 2:
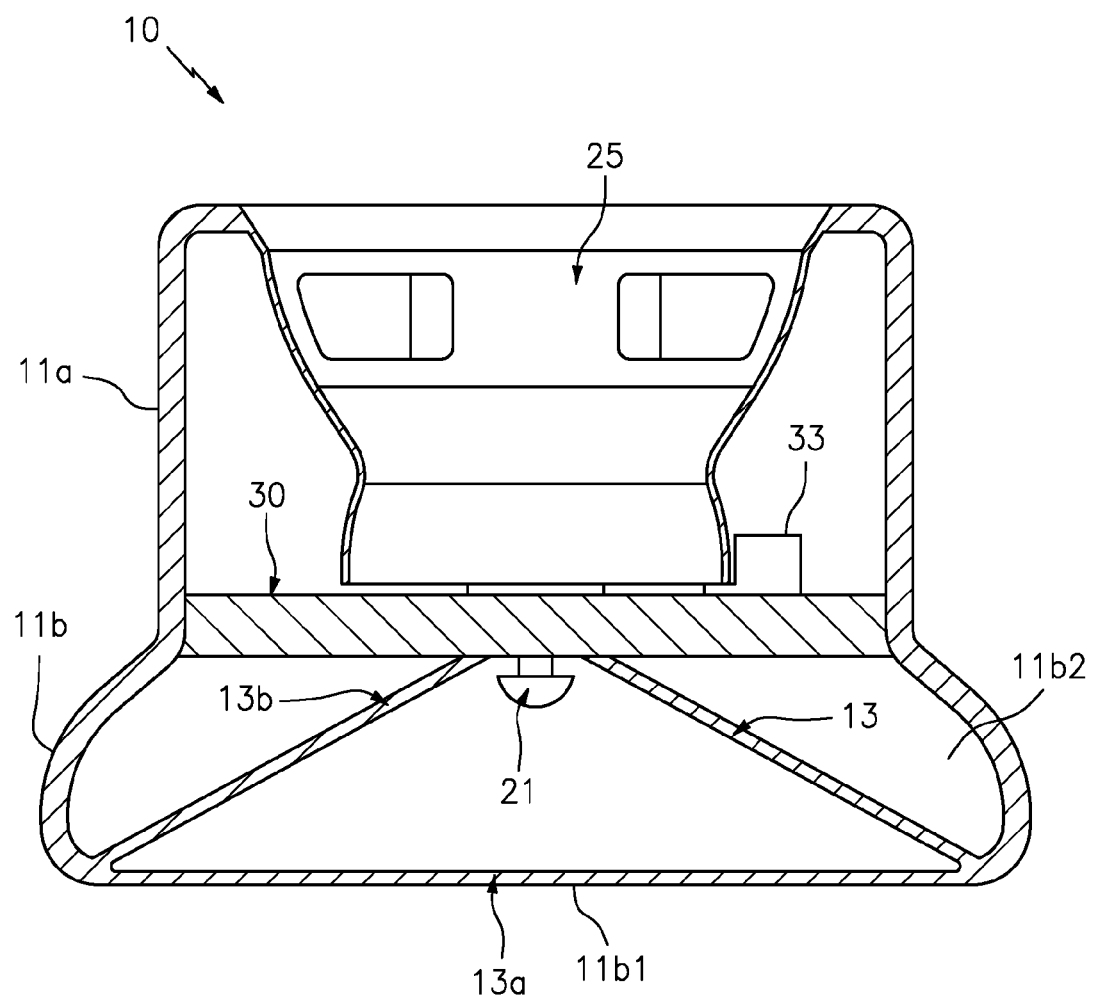
FIG. 2 is a cross sectional cutout view of the power stethoscope with integrated speaker, in accordance with one embodiment of the invention.
Figure 3:
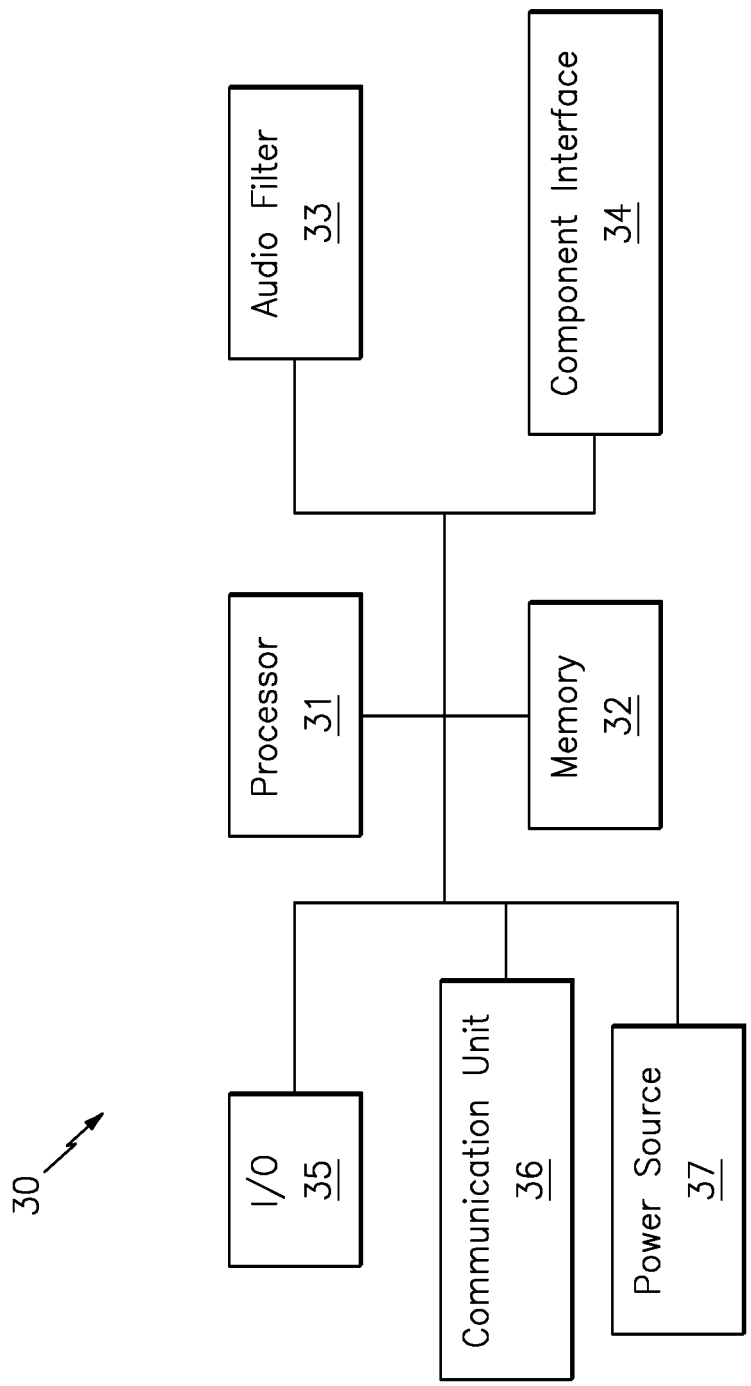
FIG. 3 is a simplified block diagram of the control unit of the power stethoscope with integrated speaker, in accordance with one embodiment of the invention.

FIGS. 1-3 illustrate one embodiment of a power stethoscope with integrated speaker device 10, that is useful for understanding the inventive concepts disclosed herein. As shown, the device 10 can include, essentially, a main body 11, one or more microphones 21, one or more speakers 25, and a control unit 30. In the preferred embodiment, each of the device components can be lined with a conductive barrier such as steel or silicone, for example, to prevent signal feedback between the components.

As shown, the main body can include an upper portion 11a, and a lower portion 11b that function to house each of the device components in a compact and moisture resistant casing, so as to allow the device to be easily carried by a practitioner without causing damage to the internal components.

In one embodiment, the upper portion 11a can include a generally tubular shape having a plurality of internal connectors (not shown) for securely positioning the control unit 30 and the speaker 25. In various embodiments, the top end of the main body can also include a speaker screen 12 or other such member for protecting the speaker without affecting the sound output of the same. Of course, the components are not limited to the illustrated arrangement, as each device component can be located along or within any portion of the main body 11.

The lower portion of the main body 11b can include a generally circular shape having a lightweight cap 11b1 along the bottom end thereof. It is particularly useful for the cap portion to be constructed from a thin (e.g., 1-2 mm) piece of smooth material such as plastic, for example, so as to allow sound waves to easily pass therethrough for capture by the microphone. Such a feature is also important as it allows the device to easily slide along the body of the patient being examined. To this end, it is noted that when the main body 11a and 11b are constructed from aluminum, the bottom cap member can be constructed from a different construction material and secured thereon in accordance with known manufacturing methodologies.

As shown best in FIG. 2, the lower portion of the main body 11b can also include a sound funnel 13 having a broad bottom end 13a that terminates against the cap 11b1, and a narrow top end 13b into which the microphone 21 can be positioned. The sound funnel can function to direct sound waves directly into the microphone for use by the control unit 30. As such, it is preferred that the sound funnel be constructed from, or lined with a dense material such as stainless steel for example, in order to prevent any sounds other than those passing through the bottom cap from entering the funnel and being detected by the microphone.

To this end, in one embodiment, the lower portion of the main body 11b can be constructed from a solid material 11b2, such as plastic, aluminum or steel, for example that extends from the outside wall of the main body 11b to the walls of the sound funnel 13. In the preferred embodiment, the solid material will be at least one inch thick. Such a thickness being important to prevent the outside sound waves from reaching the wall of the sound funnel and being subsequently captured by the microphone, while still allowing sound waves to pass through the bottom cap.

Although described and illustrated with regard to a particular shape, the main body 11 can be constructed to include any shape that is suitable for performing the functionality disclosed herein. To this end, the upper and lower portions of the main body can be constructed as two distinct elements that are joined together, or can include a unitary construction. In either instance, the main body will preferably be constructed from a nonporous and lightweight material such as aluminum, for example; however any number of other construction materials such as plastic and/or stainless steel, are also contemplated.

The microphone 21 can include any type of sound-oriented input device that can function to detect and capture sound. The speaker 25 can include any number of commercially available devices such as a cone, dome or semi-dome tweeter, for example, that can function to generate and/or play an audible sound.

FIG. 3 is a simplistic block diagram illustrating one embodiment of the control unit 30. As shown, the control unit can include a processor 31 that is conventionally connected to an internal memory 32, a digital audio filter 33, a component interface unit 34, an input/output unit 35, a communication unit 36 and/or a power source 37.

Although illustrated as separate elements, those of skill in the art will recognize that one or more system components may be, or include, one or more printed circuit boards (PCB) containing an integrated circuit or circuits for completing the activities described herein. The CPU may be one or more integrated circuits having firmware for causing the circuitry to complete the activities described herein. Of course, any number of other analogue and/or digital components capable of performing the below described functionality can be provided in place of, or in conjunction with the below described controller elements.

The processor/CPU 31 can act to execute program code stored in the memory 32 in order to allow the device to perform the functionality described herein. In various embodiments, the processor can further include a timer module that can function to accurately measure the passage of time. As described herein, the timer module can be provided as a function of the processor or can include a separate physical circuit. In either instance, processors and timers are extremely well known in the art, therefore no further description will be provided.

Memory 32 can act to store operating instructions in the form of program code for the processor 31 to execute. More specifically, the memory can provide instructions that allow the processor 31 to pass the output from the microphone 21 to the speaker 25 and/or the digital filter 33, for example.

Although illustrated in FIG. 3 as a single component, memory 32 can include one or more physical memory devices such as, for example, local memory and/or one or more bulk storage devices. As used herein, local memory can refer to random access memory or other non-persistent memory device(s) generally used during actual execution of program code, whereas a bulk storage device can be implemented as a persistent data storage device. Additionally, memory 32 can also include one or more cache memories that provide temporary storage of at least some program code in order to reduce the number of times program code must be retrieved from the bulk storage device during execution. Each of these devices are well known in the art.

In various embodiments, the memory can function to store the output of the microphone 21. Such a feature can allow a practitioner to both listen to and capture the patient sounds, such as their heart and/or lungs, for example. Such a feature can be particularly useful for a paramedic, for example, in capturing an abnormal heartbeat that is intermittent in nature. As such, upon capturing the information, the paramedic can play the sound back to the emergency room physician, and/or upload the captured sound into the patients' electronic file. Of course, any number of other uses are also contemplated.

One or more digital audio filters 33 can be communicatively linked to the processor 31, memory 32, microphone 21 and/or speaker 25. In various embodiments, the digital filter can include or comprise an amplifier which can adjust one or more of the gain, tone, amplitude and/or frequency of the microphone output, in order to allow the speaker 25 to generate a clear, accurate and distortion free audio representation of the captured patient sounds (e.g., heartbeat, lungs, etc.,).

The component interface unit 34 can function to provide a communicative link between the processor 31 and various other device components such as the speaker 25 and/or microphone 21, for example. In this regard, the component interface unit can include any number of different components such as one or more PIC microcontrollers, internal bus, USB connections and other such hardware capable of providing a direct link between the various components. Of course any other means for providing the two way communication between the identified components can also be utilized herein.

The input/output unit 35 can be provided to accept user inputs and/or to provide operating information to a device user. In various embodiments, the input/output unit can include or control one or more buttons/switches 35*a*, that are connected to the processor 31 so as to activate various programmatic functions, e.g., speaker volume, on, off, record, etc. The input/output unit can also include or control any number of lights 35*b* so as to clearly indicate whether the device is in the ON, OFF and/or recording operating state, for example. In addition to the above, the input/output unit can also include or control a headphone jack 35*c* for receiving a pair of conventional earphones/earbuds, or an audio plug from an external speaker system, for example, so as to allow a device user to listen to the microphone output.

The communication unit 36 can include any number of devices capable of communicating with an external device either directly or over a network. In one preferred embodiment, the communication unit can include one or more communication ports such as a Universal Serial Bus (USB) 36*a*, for example, in order to send and receive information with another device via a direct communication link. In another embodiment, the communication unit can also include a Bluetooth transceiver for communicating wirelessly with an external device such as a smartphone, computer and/or tablet device running an App.

Of course, the inventive concepts are not limiting to any particular communication component, as any number of other known transmission and reception mechanisms and protocols can also be utilized herein, several nonlimiting examples include unique radio frequencies, infrared (IR), RFID, and/or a network adapter functioning to communicate over a WAN, LAN or the internet via an internet service provider, for example.

In one preferred embodiment, the power source 37 can include one or more DC batteries capable of providing the necessary power requirements to each element of the device 10. In one embodiment, the batteries can be permanently located within the main body and can be rechargeable in nature via the communication port 35*d*, for example. Of course, other embodiments are contemplated wherein the main body includes a battery compartment having a removable cover (not illustrated) for receiving non-rechargeable batteries.

The power stethoscope 10 can be used in the expected manner, wherein a device user places the bottom end cap 11*b*1 of the main body against a portion of a patient's body. When so positioned, patient sounds can be funneled to the microphone, whose output can then be filtered and/or amplified before being broadcast by the integrated speaker. To this end, the device user can adjust the volume of the speaker output to suit a particular operating environment, and can also record the captured information for playback or uploading at a later time. Moreover, the device can also be communicatively linked to external speakers so as to allow the patients vital sounds to be broadcast to any number of other individuals. Such a feature is particularly beneficial in a teaching situation.

As described herein, one or more elements of the power stethoscope 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individual elements such as the upper and lower portions of the main body, for example, may be formed together as one continuous element, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A power stethoscope device, comprising:
   a compact and unitary main body having an upper portion and a lower portion;
   a sound funnel that is disposed within the lower portion of the unitary main body, said sound funnel being constructed from a dense material for preventing sounds from passing therethrough, and comprising a narrow top end, a hollow middle portion, and a broad bottom end;
   a microphone that is configured to capture sounds entering the sound funnel, said microphone being positioned inside the hollow middle portion of the sound funnel at a location adjacent to the narrow top end;
   a speaker that is disposed within the upper portion of the unitary main body and is communicatively linked to the microphone, said speaker functioning to broadcast an output of the microphone; and
   a sound isolating material that is disposed along an entirety of the lower portion of the unitary main body between the sound funnel and an outside facing surface of the unitary main body.

2. The device of claim 1, further comprising:
   a cap that is positioned along the bottom end of the main body, said cap being constructed from a thin piece of plastic to allow sound waves to pass therethrough.

3. The device of claim 1, further comprising:
   a control unit that is communicatively linked to the speaker and the microphone, said control unit including:
   a memory configured to store operating instructions;
   an input/output unit configured to receive and display user information;

a power source; and a processor that is in communication with each of the memory, the input/output unit, and the power source.

4. The device of claim 3, further comprising:

a digital audio filter that is in communication with each of the microphone, the speaker and the processor, said filter being configured to adjust at least one of a gain, a tone, an amplitude and a frequency of an output of the microphone.

5. The device of claim 3, further comprising:

a communication unit that is positioned along the main body and is communicatively linked to the control unit, and wherein said memory is further configured to record an output of the microphone, and to transmit the same via the communication unit.

6. The device of claim 5, wherein the communication unit includes a Universal Serial Bus connector.

7. The device of claim 5 wherein the communication unit comprises a wireless communicator.

8. The device of claim 7, wherein the wireless communicator includes a Bluetooth transceiver.

9. The device of claim 7, wherein the control unit includes functionality for broadcasting the output of the microphone via the speaker; and transmitting the output of the microphone via the wireless communicator.

10. The device of claim 7, further comprising:

a headphone jack that is configured to transmit the output of the microphone to an external device.

11. The device of claim 10, wherein the control unit includes functionality for transmitting the output of the microphone via the headphone jack; and transmitting the output of the microphone via the wireless communicator.

12. A power stethoscope device, consisting of:

a compact and unitary main body having an upper portion and a lower portion;

a sound funnel that is disposed within the lower portion of the unitary main body, said sound funnel being constructed from a dense material for preventing sounds from passing therethrough, and comprising a narrow top end, a hollow middle portion, and a broad bottom end;

a microphone that is configured to capture sounds entering the sound funnel, said microphone being positioned inside the hollow middle portion of the sound funnel at a location adjacent to the narrow top end;

a speaker that is disposed within the upper portion of the unitary main body and is communicatively linked to the microphone, said speaker functioning to broadcast an output of the microphone; and a sound isolating material that is disposed along an entirety of the lower portion of the unitary main body between the sound funnel and an outside facing surface of the unitary main body.

* * * * *